US012663771B2

(12) United States Patent
    Prochnow

(10) Patent No.:     US 12,663,771 B2
(45) Date of Patent:        Jun. 23, 2026

(54) REMOTE MONITORING SYSTEMS AND METHODS

(71) Applicant: Boone Cable Works & Electronics, Inc., Boone, IA (US)

(72) Inventor: Michael R. Prochnow, Madrid, IA (US)

(73) Assignee: BOONE CABLE WORKS & ELECTRONICS, INC., Boone, IA (US)

( * ) Notice: Subject to any disclaimer, the term of this patent is extended or adjusted under 35 U.S.C. 154(b) by 433 days.

(21) Appl. No.: 18/496,363

(22) Filed: Oct. 27, 2023

(65) Prior Publication Data

US 2024/0142927 A1      May 2, 2024

Related U.S. Application Data

(60) Provisional application No. 63/421,370, filed on Nov. 1, 2022.

(51) Int. Cl.
    *G05B 19/04*      (2006.01)
    *G01K 1/024*      (2021.01)
    *G01K 7/02*       (2021.01)
    *G01K 13/02*      (2021.01)
    *G01K 13/10*      (2006.01)
    *G01N 33/02*      (2006.01)
    *G05B 19/042*     (2006.01)

(52) U.S. Cl.
    CPC ........... *G05B 19/041* (2013.01); *G01K 1/024* (2013.01); *G01K 7/023* (2013.01); *G01K 13/02* (2013.01); *G01K 13/10* (2013.01);

*G05B 19/042* (2013.01); *G01K 2219/00* (2013.01); *G01N 33/02* (2013.01); *G05B 2219/14043* (2013.01)

(58) Field of Classification Search
    None
    See application file for complete search history.

(56) References Cited

U.S. PATENT DOCUMENTS

| | | | | |
|---|---|---|---|---|
| 5,166,926 | A * | 11/1992 | Cisneros | H04L 12/5601 370/399 |
| 8,138,972 | B2 * | 3/2012 | Underbrink | H04B 1/707 342/357.63 |
| 9,429,478 | B2 | 8/2016 | Honeck et al. | |

(Continued)

FOREIGN PATENT DOCUMENTS

| | | |
|---|---|---|
| CA | 3087717 A1 | 9/2019 |
| CA | 3160495 A1 | 5/2021 |

(Continued)

OTHER PUBLICATIONS

Applicant: Boone Cable Works & Electronics, Inc.; "Remote Monitoring Systems and Methods"; Canadian Application No. 3,218,243; Canadian Office Action dated Aug. 28, 2025; 4 pgs.

*Primary Examiner* — Kevin R Steckbauer

(74) *Attorney, Agent, or Firm* — Tarolli, Sundheim, Covell & Tummino LLP

(57) ABSTRACT

This disclosure relates to remote monitoring systems and methods, such as for monitoring the condition of bulk solids, such as agricultural grain, pelletized materials and/or equipment. The systems and methods described herein integrate analog and digital monitoring technologies and enable such technologies to be managed and controlled by one or more users.

20 Claims, 3 Drawing Sheets

(56) References Cited

U.S. PATENT DOCUMENTS

| | | | | |
|---|---|---|---|---|
| 10,296,863 | B2 | 5/2019 | Bantas et al. | |
| 10,399,106 | B2 | 9/2019 | Dudar | |
| 10,557,640 | B2* | 2/2020 | Warren | G01R 19/16533 |
| 10,652,723 | B2 | 5/2020 | Dames et al. | |
| 10,712,738 | B2* | 7/2020 | Cella | G05B 19/4185 |
| 10,732,621 | B2* | 8/2020 | Cella | G05B 19/4185 |
| 10,754,334 | B2* | 8/2020 | Cella | G05B 19/4185 |
| 10,866,584 | B2* | 12/2020 | Cella | G05B 19/4185 |
| 10,983,514 | B2* | 4/2021 | Cella | G05B 19/4185 |
| 11,003,179 | B2* | 5/2021 | Cella | G05B 19/4185 |
| 11,009,865 | B2* | 5/2021 | Cella | G05B 19/4185 |
| 11,029,680 | B2* | 6/2021 | Cella | G05B 19/4185 |
| 11,048,248 | B2* | 6/2021 | Cella | G05B 19/4185 |
| 11,054,817 | B2* | 7/2021 | Cella | G05B 19/4185 |
| 11,073,826 | B2* | 7/2021 | Cella | G05B 19/4185 |
| 11,086,311 | B2* | 8/2021 | Cella | G05B 19/4185 |
| 11,106,199 | B2* | 8/2021 | Cella | G05B 19/4185 |
| 11,112,784 | B2* | 9/2021 | Cella | G05B 19/4185 |
| 11,112,785 | B2* | 9/2021 | Cella | G05B 19/4185 |
| 11,119,473 | B2* | 9/2021 | Cella | G05B 19/4185 |
| 11,126,171 | B2* | 9/2021 | Cella | G05B 19/4185 |
| 11,137,752 | B2* | 10/2021 | Cella | G05B 19/4185 |
| 11,156,998 | B2* | 10/2021 | Cella | G05B 19/4185 |
| 11,169,511 | B2* | 11/2021 | Cella | G05B 19/4185 |
| 11,181,893 | B2* | 11/2021 | Cella | G05B 19/4185 |
| 11,194,319 | B2* | 12/2021 | Cella | G05B 19/4185 |
| 11,199,835 | B2* | 12/2021 | Cella | G05B 19/4185 |
| 11,199,837 | B2* | 12/2021 | Cella | G05B 19/0425 |
| 11,215,980 | B2* | 1/2022 | Cella | G05B 19/4183 |
| 11,243,521 | B2* | 2/2022 | Cella | G05B 19/4183 |
| 11,243,522 | B2* | 2/2022 | Cella | G05B 19/4183 |
| 11,243,528 | B2* | 2/2022 | Cella | G05B 19/4183 |
| 11,256,242 | B2* | 2/2022 | Cella | G05B 19/4183 |
| 11,256,243 | B2* | 2/2022 | Cella | G05B 19/4183 |
| 11,269,318 | B2* | 3/2022 | Cella | G05B 19/4183 |
| 11,269,319 | B2* | 3/2022 | Cella | G05B 19/4183 |
| 11,307,062 | B2 | 4/2022 | Zafar et al. | |
| 11,307,565 | B2* | 4/2022 | Cella | G05B 19/4183 |
| 11,334,063 | B2* | 5/2022 | Cella | G05B 19/4183 |
| 11,340,589 | B2* | 5/2022 | Cella | G05B 19/4183 |
| 11,347,205 | B2* | 5/2022 | Cella | G05B 19/4183 |
| 11,347,206 | B2* | 5/2022 | Cella | G05B 19/4183 |
| 11,347,215 | B2* | 5/2022 | Cella | G05B 19/4183 |
| 11,353,850 | B2* | 6/2022 | Cella | G05B 19/4185 |
| 11,353,851 | B2* | 6/2022 | Cella | G05B 19/4185 |
| 11,360,459 | B2* | 6/2022 | Cella | G05B 19/4185 |
| 11,366,455 | B2* | 6/2022 | Cella | G05B 19/4185 |
| 11,366,456 | B2* | 6/2022 | Cella | G05B 19/4185 |
| 11,372,394 | B2* | 6/2022 | Cella | G05B 19/4185 |
| 11,372,395 | B2* | 6/2022 | Cella | G05B 19/4185 |
| 11,378,938 | B2* | 7/2022 | Cella | G05B 19/4185 |
| 11,385,622 | B2* | 7/2022 | Cella | G05B 19/4185 |
| 11,385,623 | B2* | 7/2022 | Cella | G05B 19/4185 |
| 11,392,109 | B2* | 7/2022 | Cella | G05B 19/4185 |
| 11,392,111 | B2* | 7/2022 | Cella | G05B 19/4185 |
| 11,392,116 | B2* | 7/2022 | Cella | G05B 19/4183 |
| 11,397,421 | B2* | 7/2022 | Cella | G05B 19/4185 |
| 11,397,422 | B2* | 7/2022 | Cella | G05B 19/4185 |
| 11,402,826 | B2* | 8/2022 | Cella | G05B 19/4185 |
| 11,409,266 | B2* | 8/2022 | Cella | G05B 19/4185 |
| 11,415,978 | B2* | 8/2022 | Cella | G05B 19/4183 |
| 11,493,903 | B2* | 11/2022 | Cella | G05B 19/4185 |
| 11,507,064 | B2* | 11/2022 | Cella | G05B 19/4185 |
| 11,507,075 | B2* | 11/2022 | Cella | G05B 19/4185 |
| 11,573,557 | B2* | 2/2023 | Cella | G05B 19/4185 |
| 11,573,558 | B2* | 2/2023 | Cella | G05B 19/4185 |
| 11,586,181 | B2* | 2/2023 | Cella | G05B 19/4185 |
| 11,586,188 | B2* | 2/2023 | Cella | G05B 19/4185 |
| 11,609,552 | B2* | 3/2023 | Cella | G05B 19/4185 |
| 11,609,553 | B2* | 3/2023 | Cella | G05B 19/4185 |
| 11,646,808 | B2* | 5/2023 | Cella | G05B 19/4185 |
| | | | | 702/188 |
| 11,663,442 | B2* | 5/2023 | Cella | G05B 19/4183 |
| | | | | 702/188 |
| 11,728,910 | B2* | 8/2023 | Cella | G05B 19/4185 |
| | | | | 702/188 |
| 11,755,878 | B2* | 9/2023 | Cella | G05B 19/4183 |
| | | | | 702/188 |
| 11,791,914 | B2* | 10/2023 | Cella | G05B 19/4185 |
| | | | | 702/188 |
| 11,836,571 | B2* | 12/2023 | Cella | G05B 19/4183 |
| 11,838,036 | B2* | 12/2023 | Cella | G05B 19/4185 |
| 11,996,900 | B2* | 5/2024 | Cella | G05B 19/4185 |
| 12,039,426 | B2* | 7/2024 | Cella | G05B 19/4183 |
| 12,099,911 | B2* | 9/2024 | Cella | G05B 19/4183 |
| 12,237,873 | B2* | 2/2025 | Cella | G05B 19/4185 |
| 12,244,359 | B2* | 3/2025 | Cella | G05B 19/4185 |
| 12,282,837 | B2* | 4/2025 | Cella | G05B 19/4183 |
| 12,327,168 | B2* | 6/2025 | Cella | G05B 19/4183 |
| 12,333,401 | B2* | 6/2025 | Cella | G05B 19/4183 |
| 12,333,402 | B2* | 6/2025 | Cella | G05B 19/4183 |
| 12,333,403 | B2* | 6/2025 | Cella | G05B 19/4183 |
| 12,372,946 | B2* | 7/2025 | Cella | G05B 19/4183 |
| 12,535,801 | B2* | 1/2026 | Cella | H04B 17/29 |
| 2011/0102258 | A1* | 5/2011 | Underbrink | G01S 19/37 |
| | | | | 342/357.47 |
| 2018/0284735 | A1* | 10/2018 | Cella | G05B 19/4185 |
| 2018/0284736 | A1* | 10/2018 | Cella | G05B 19/4185 |
| 2018/0284737 | A1* | 10/2018 | Cella | G05B 19/4185 |
| 2018/0284741 | A1* | 10/2018 | Cella | G05B 19/4185 |
| 2018/0284742 | A1* | 10/2018 | Cella | G05B 19/4185 |
| 2018/0284743 | A1* | 10/2018 | Cella | G05B 19/4185 |
| 2018/0284744 | A1* | 10/2018 | Cella | G05B 19/4185 |
| 2018/0284745 | A1* | 10/2018 | Cella | G05B 19/4185 |
| 2018/0284746 | A1* | 10/2018 | Cella | G05B 19/4185 |
| 2018/0284747 | A1* | 10/2018 | Cella | G05B 19/4185 |
| 2018/0284749 | A1* | 10/2018 | Cella | G05B 19/4185 |
| 2018/0284752 | A1* | 10/2018 | Cella | G05B 19/4185 |
| 2018/0284753 | A1* | 10/2018 | Cella | G05B 19/4185 |
| 2018/0284754 | A1* | 10/2018 | Cella | G05B 19/4185 |
| 2018/0284755 | A1* | 10/2018 | Cella | G05B 19/4185 |
| 2018/0284756 | A1* | 10/2018 | Cella | G05B 19/4185 |
| 2018/0284757 | A1* | 10/2018 | Cella | G05B 19/4185 |
| 2018/0284758 | A1* | 10/2018 | Cella | G05B 19/4185 |
| 2018/0299878 | A1* | 10/2018 | Cella | G05B 19/4185 |
| 2018/0321666 | A1* | 11/2018 | Cella | G05B 19/4185 |
| 2018/0321667 | A1* | 11/2018 | Cella | G05B 19/4185 |
| 2018/0321672 | A1* | 11/2018 | Cella | G05B 19/4185 |
| 2019/0025805 | A1* | 1/2019 | Cella | G05B 19/4185 |
| 2019/0025806 | A1* | 1/2019 | Cella | G05B 19/4185 |
| 2019/0033845 | A1* | 1/2019 | Cella | G05B 19/4185 |
| 2019/0033846 | A1* | 1/2019 | Cella | G05B 19/4185 |
| 2019/0033847 | A1* | 1/2019 | Cella | G05B 19/4185 |
| 2019/0033848 | A1* | 1/2019 | Cella | G05B 19/4185 |
| 2019/0041835 | A1* | 2/2019 | Cella | G05B 19/4183 |
| 2019/0041836 | A1* | 2/2019 | Cella | G05B 19/4185 |
| 2019/0041840 | A1* | 2/2019 | Cella | G05B 19/4185 |
| 2019/0041841 | A1* | 2/2019 | Cella | G05B 19/4185 |
| 2019/0041842 | A1* | 2/2019 | Cella | G05B 19/4183 |
| 2019/0041843 | A1* | 2/2019 | Cella | G05B 19/4185 |
| 2019/0041845 | A1* | 2/2019 | Cella | G05B 19/4185 |
| 2019/0041846 | A1* | 2/2019 | Cella | G05B 19/4185 |
| 2019/0056132 | A1* | 2/2019 | Warren | F24F 11/62 |
| 2019/0064791 | A1* | 2/2019 | Cella | G05B 19/4183 |
| 2019/0064792 | A1* | 2/2019 | Cella | G05B 19/4185 |
| 2019/0121333 | A1* | 4/2019 | Cella | G05B 19/4183 |
| 2019/0121338 | A1* | 4/2019 | Cella | G05B 19/4183 |
| 2019/0121339 | A1* | 4/2019 | Cella | G05B 19/4185 |
| 2019/0121340 | A1* | 4/2019 | Cella | G05B 19/4185 |
| 2019/0121341 | A1* | 4/2019 | Cella | G05B 19/4183 |
| 2019/0121343 | A1* | 4/2019 | Cella | G05B 19/4185 |
| 2019/0121344 | A1* | 4/2019 | Cella | G05B 19/4185 |
| 2019/0121345 | A1* | 4/2019 | Cella | G05B 19/4185 |
| 2019/0121346 | A1* | 4/2019 | Cella | G05B 19/4185 |
| 2019/0121349 | A1* | 4/2019 | Cella | G05B 19/4185 |
| 2019/0121350 | A1* | 4/2019 | Cella | G05B 19/4183 |
| 2019/0129404 | A1* | 5/2019 | Cella | G05B 19/4185 |
| 2019/0129405 | A1* | 5/2019 | Cella | G05B 19/4185 |
| 2019/0129406 | A1* | 5/2019 | Cella | G05B 19/4185 |
| 2019/0129407 | A1* | 5/2019 | Cella | G05B 19/4183 |
| 2019/0129408 | A1* | 5/2019 | Cella | G05B 19/4185 |
| 2019/0129409 | A1* | 5/2019 | Cella | G05B 19/4185 |
| 2019/0129410 | A1* | 5/2019 | Cella | G05B 19/4183 |

(56) References Cited

U.S. PATENT DOCUMENTS

| | | | | |
|---|---|---|---|---|
| 2019/0137985 A1* | 5/2019 | Cella | ......... | G05B 19/4185 |
| 2019/0137987 A1* | 5/2019 | Cella | ......... | G05B 19/4185 |
| 2019/0137988 A1* | 5/2019 | Cella | ......... | G05B 19/4185 |
| 2019/0137989 A1* | 5/2019 | Cella | ......... | G05B 19/4185 |
| 2019/0146472 A1* | 5/2019 | Cella | ......... | G05B 19/4183 |
| | | | | 702/188 |
| 2019/0146473 A1* | 5/2019 | Cella | ......... | G05B 19/4183 |
| | | | | 702/188 |
| 2019/0146474 A1* | 5/2019 | Cella | ......... | G05B 19/4183 |
| | | | | 702/188 |
| 2019/0146475 A1* | 5/2019 | Cella | ......... | G05B 19/4183 |
| | | | | 702/188 |
| 2019/0146476 A1* | 5/2019 | Cella | ......... | G05B 19/4185 |
| | | | | 702/188 |
| 2019/0146477 A1* | 5/2019 | Cella | ......... | G05B 19/4185 |
| | | | | 702/188 |
| 2019/0146478 A1* | 5/2019 | Cella | ......... | G05B 19/4183 |
| | | | | 702/188 |
| 2019/0146479 A1* | 5/2019 | Cella | ......... | G05B 19/4183 |
| | | | | 702/188 |
| 2019/0146480 A1* | 5/2019 | Cella | ......... | G05B 19/4183 |
| | | | | 702/188 |
| 2019/0146481 A1* | 5/2019 | Cella | ......... | G05B 19/4185 |
| | | | | 702/188 |
| 2019/0146482 A1* | 5/2019 | Cella | ......... | G05B 19/4185 |
| | | | | 702/188 |
| 2019/0155263 A1* | 5/2019 | Cella | ......... | G05B 19/4183 |
| 2019/0155272 A1* | 5/2019 | Cella | ......... | G05B 19/4185 |
| 2019/0179300 A1* | 6/2019 | Cella | ......... | G05B 19/4185 |
| 2019/0179301 A1* | 6/2019 | Cella | ......... | G05B 19/4185 |
| 2019/0187680 A1* | 6/2019 | Cella | ......... | G05B 19/4185 |
| 2019/0187681 A1* | 6/2019 | Cella | ......... | G05B 19/4185 |
| 2019/0187682 A1* | 6/2019 | Cella | ......... | G05B 19/4185 |
| 2019/0187683 A1* | 6/2019 | Cella | ......... | G05B 19/4185 |
| 2019/0187684 A1* | 6/2019 | Cella | ......... | G05B 19/4185 |
| 2019/0187685 A1* | 6/2019 | Cella | ......... | G05B 19/4185 |
| 2019/0187686 A1* | 6/2019 | Cella | ......... | G05B 19/4185 |
| 2019/0187687 A1* | 6/2019 | Cella | ......... | G05B 19/4185 |
| 2019/0187688 A1* | 6/2019 | Cella | ......... | G05B 19/4185 |
| 2019/0187689 A1* | 6/2019 | Cella | ......... | G05B 19/4185 |
| 2019/0187690 A1* | 6/2019 | Cella | ......... | G05B 19/4185 |
| 2019/0219995 A1* | 7/2019 | Cella | ......... | G05B 19/4185 |
| 2019/0219996 A1* | 7/2019 | Cella | ......... | G05B 19/4185 |
| 2019/0227536 A1* | 7/2019 | Cella | ......... | G05B 19/4185 |
| 2019/0227537 A1* | 7/2019 | Cella | ......... | G05B 19/4185 |
| 2019/0324431 A1* | 10/2019 | Cella | ......... | G05B 19/0425 |
| 2019/0339684 A1* | 11/2019 | Cella | ......... | G05B 19/4185 |
| 2019/0339685 A1* | 11/2019 | Cella | ......... | G05B 19/4185 |
| 2019/0339686 A1* | 11/2019 | Cella | ......... | G05B 19/4185 |
| 2019/0339687 A1* | 11/2019 | Cella | ......... | G05B 19/4185 |
| 2020/0019154 A1* | 1/2020 | Cella | ......... | G05B 19/4185 |
| 2020/0019155 A1* | 1/2020 | Cella | ......... | G05B 19/4185 |
| 2020/0026270 A1* | 1/2020 | Cella | ......... | G05B 19/4185 |
| 2020/0096986 A1* | 3/2020 | Cella | ......... | G05B 19/4185 |
| 2020/0096989 A1* | 3/2020 | Cella | ......... | G05B 19/4185 |
| 2020/0096991 A1* | 3/2020 | Cella | ......... | G05B 19/4183 |
| 2020/0096992 A1* | 3/2020 | Cella | ......... | G05B 19/4185 |
| 2020/0096993 A1* | 3/2020 | Cella | ......... | G05B 19/4185 |
| 2020/0096994 A1* | 3/2020 | Cella | ......... | G05B 19/4185 |
| 2020/0096995 A1* | 3/2020 | Cella | ......... | G05B 19/4185 |
| 2020/0096996 A1* | 3/2020 | Cella | ......... | G05B 19/4185 |
| 2020/0096997 A1* | 3/2020 | Cella | ......... | G05B 19/4185 |
| 2020/0096998 A1* | 3/2020 | Cella | ......... | G05B 19/4185 |
| 2020/0103889 A1* | 4/2020 | Cella | ......... | G05B 19/4183 |
| 2020/0103890 A1* | 4/2020 | Cella | ......... | G05B 19/4185 |
| 2020/0103891 A1* | 4/2020 | Cella | ......... | G05B 19/4185 |
| 2020/0103892 A1* | 4/2020 | Cella | ......... | G05B 19/4185 |
| 2020/0103893 A1* | 4/2020 | Cella | ......... | G05B 19/4185 |
| 2020/0110397 A1* | 4/2020 | Cella | ......... | G05B 19/4183 |
| 2020/0110398 A1* | 4/2020 | Cella | ......... | G05B 19/4185 |
| 2020/0110399 A1* | 4/2020 | Cella | ......... | G05B 19/4185 |
| 2020/0110400 A1* | 4/2020 | Cella | ......... | G05B 19/4185 |
| 2020/0348662 A1* | 11/2020 | Cella | ......... | G05B 23/0294 |
| 2021/0003429 A1 | 1/2021 | Zafar et al. | | |
| 2021/0123896 A1 | 4/2021 | Barrettino | | |
| 2021/0144802 A1 | 5/2021 | Zafar et al. | | |
| 2021/0157312 A1* | 5/2021 | Cella | ......... | G06Q 30/06 |
| 2022/0083046 A1* | 3/2022 | Cella | ......... | G05B 23/0294 |
| 2022/0083047 A1* | 3/2022 | Cella | ......... | G05B 23/0294 |
| 2022/0083048 A1* | 3/2022 | Cella | ......... | G05B 23/0294 |
| 2022/0163959 A1* | 5/2022 | Cella | ......... | G06Q 30/06 |
| 2022/0163960 A1* | 5/2022 | Cella | ......... | G06Q 30/06 |
| 2022/0187822 A1* | 6/2022 | Cella | ......... | G05B 19/4183 |
| 2022/0236086 A1 | 7/2022 | Zafar | | |
| 2022/0326690 A1* | 10/2022 | Cella | ......... | G05B 19/4183 |
| 2023/0089205 A1* | 3/2023 | Cella | ......... | G06Q 30/06 |
| | | | | 702/188 |
| 2023/0092066 A1* | 3/2023 | Cella | ......... | G06Q 30/06 |
| | | | | 702/188 |
| 2023/0098519 A1* | 3/2023 | Cella | ......... | G06Q 30/06 |
| | | | | 702/188 |
| 2023/0099267 A1* | 3/2023 | Cella | ......... | G05B 19/4183 |
| | | | | 702/188 |
| 2023/0104612 A1* | 4/2023 | Cella | ......... | G05B 19/4183 |
| | | | | 702/188 |
| 2023/0108981 A1* | 4/2023 | Cella | ......... | G05B 19/4183 |
| | | | | 702/188 |
| 2023/0109195 A1* | 4/2023 | Cella | ......... | G05B 19/4183 |
| | | | | 702/188 |
| 2023/0111071 A1* | 4/2023 | Cella | ......... | G06Q 30/06 |
| | | | | 702/188 |
| 2023/0111673 A1* | 4/2023 | Cella | ......... | G05B 19/4183 |
| | | | | 702/188 |
| 2023/0111829 A1* | 4/2023 | Cella | ......... | G05B 19/4183 |
| | | | | 702/188 |
| 2023/0135882 A1* | 5/2023 | Cella | ......... | G06Q 30/06 |
| | | | | 702/188 |
| 2023/0196230 A1* | 6/2023 | Cella | ......... | G06V 10/82 |
| | | | | 705/7.17 |
| 2023/0273600 A1* | 8/2023 | Cella | ......... | G05B 19/4183 |
| | | | | 702/188 |
| 2023/0297807 A1* | 9/2023 | Cella | ......... | G05B 19/4183 |
| | | | | 702/188 |
| 2023/0385598 A1* | 11/2023 | Cella | ......... | G05B 19/4183 |
| 2023/0401418 A1* | 12/2023 | Cella | ......... | G05B 19/4183 |
| 2023/0403087 A1* | 12/2023 | Cella | ......... | G05B 19/4183 |
| 2023/0409866 A1* | 12/2023 | Cella | ......... | G05B 19/4183 |
| 2024/0142927 A1* | 5/2024 | Prochnow | ......... | G01K 7/023 |
| 2024/0214086 A1* | 6/2024 | Cella | ......... | G05B 19/4183 |
| 2024/0396647 A1* | 11/2024 | Cella | ......... | G05B 19/4183 |
| 2025/0148259 A1* | 5/2025 | Cella | ......... | G05B 19/4183 |
| 2025/0181253 A1* | 6/2025 | Cella | ......... | G05B 19/4185 |

FOREIGN PATENT DOCUMENTS

| | | | | | |
|---|---|---|---|---|---|
| CN | 103543700 B | * | 8/2016 | | |
| CN | 110325929 A | * | 10/2019 | ......... | H04L 63/1416 |
| DE | 102022122048 A1 | * | 2/2024 | ......... | H04L 1/0083 |
| DE | 102022122048 B4 | * | 7/2024 | ......... | H04L 49/104 |
| EP | 3759937 A2 | | 1/2021 | | |
| EP | 4055542 A1 | | 9/2022 | | |
| JP | 2019523425 A | * | 8/2019 | ......... | G05B 23/0221 |
| JP | 2022078082 A | * | 5/2022 | ......... | G06N 3/042 |
| JP | 2024019175 A | * | 2/2024 | ......... | G05B 19/0423 |
| JP | 7454160 B2 | * | 3/2024 | ......... | G05B 19/0423 |
| KR | 20230157525 A | * | 11/2013 | ......... | G05B 19/0423 |
| KR | 20180135089 A | * | 12/2018 | ......... | G05B 23/0221 |
| KR | 20190075160 A | * | 6/2019 | ......... | G05B 23/0221 |
| KR | 102000416 B1 | * | 7/2019 | ......... | G05B 23/0221 |
| KR | 102599073 B1 | * | 11/2023 | ......... | G05B 19/0423 |

* cited by examiner

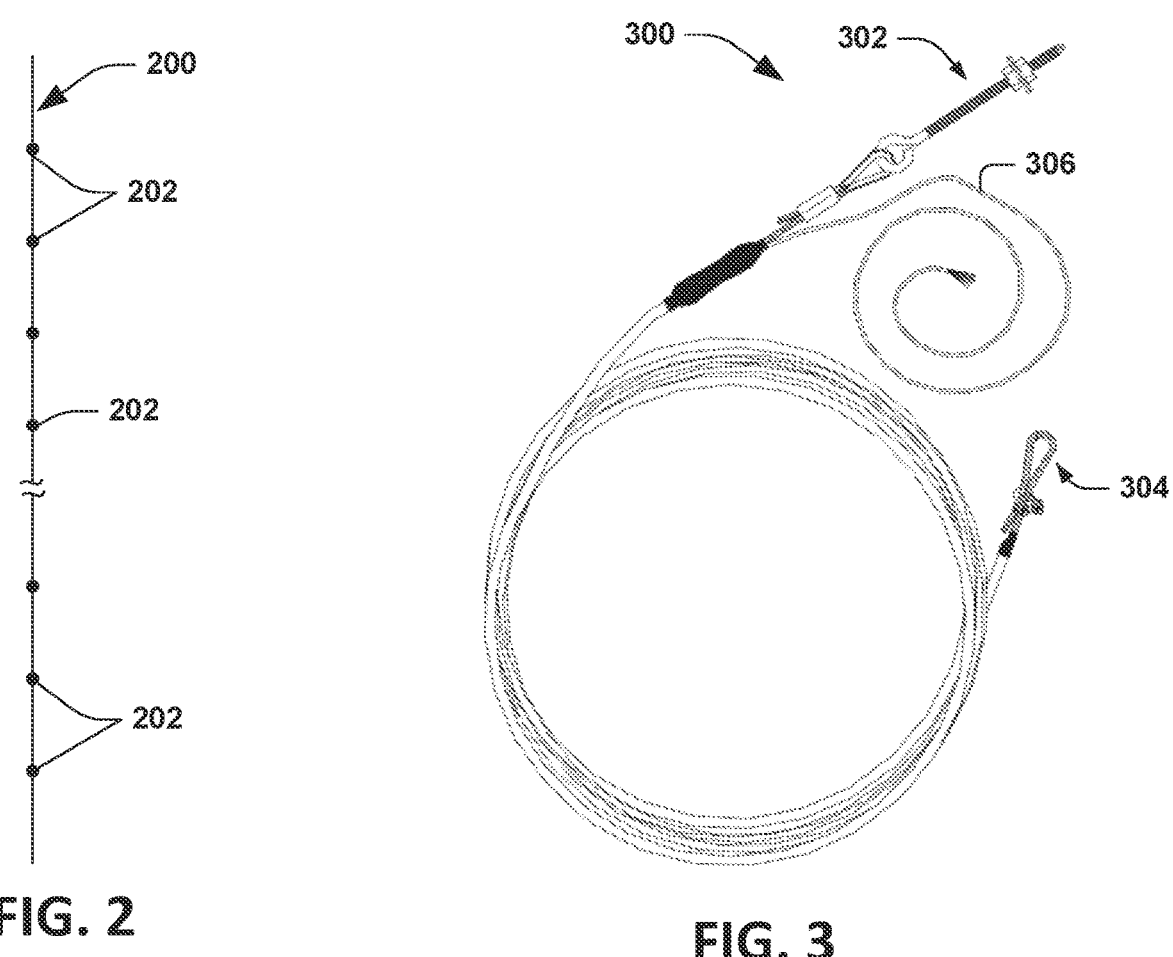
FIG. 2
FIG. 3
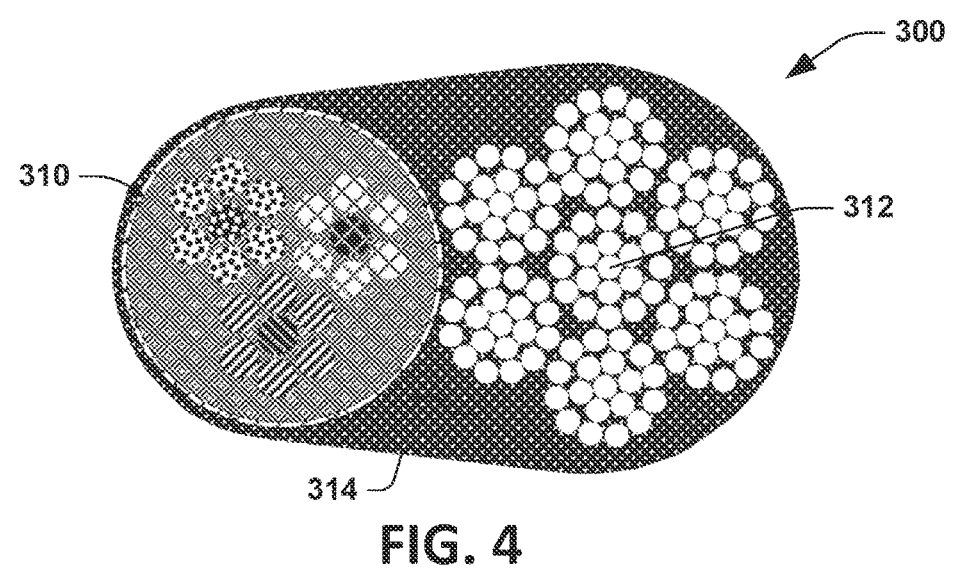
FIG. 4

REMOTE MONITORING SYSTEMS AND METHODS

CROSS-REFERENCE TO RELATED APPLICATION

This application claims priority to U.S. Provisional Patent application No. 63/421,370, filed Nov. 1, 2022, which is incorporated herein by reference in its entirety.

TECHNICAL FIELD

This disclosure relates to a remote sensing system and method, such as for monitoring the condition of stored agricultural products and equipment.

BACKGROUND

In the farming and agricultural industries, large quantities of bulk solids, such as agricultural grain and pelletized materials (e.g., feed, wood pellets, and fertilizer), are often stored in bins, bunkers or other storage facilities. Devices and systems have been developed to monitor one or more conditions of such materials, including temperature and moisture. For example, if grain has a moisture content above a certain amount, it can create an environment conducive to insect and fungal growth and development. Also, grain left unmanaged may increase in temperature and subsequent convection currents can cause surface condensation or other adverse conditions.

SUMMARY

This disclosure relates to a remote sensing system and method, such as for monitoring the condition of stored agricultural products and equipment.

As one example, a monitoring system includes a gateway having at least one interface configured to communicate information and commands. A computing apparatus is in communication with the gateway and configured to send commands to and receive information from the gateway. An analog monitoring circuit includes a first data link interface, a first controller, a driver network, an analog-to-digital converter, and a switch network. The first data link interface is coupled to the gateway interface to provide bidirectional communication of data. The first controller includes a first link terminal, a group address terminal, a switch select terminal and a data terminal, in which the first link terminal is coupled to the first data link interface. A driver network includes a plurality of driver outputs and an address input terminal, in which the address input terminal is coupled to the group address terminal. The analog-to-digital converter includes an analog input and a digital output, in which the digital output is coupled to the data terminal. The switch network has a switch address terminal and a plurality of analog sensor terminals, and the switch network includes a plurality of switches coupled between the analog input and the analog sensor terminals. The switch address terminal is coupled to the switch select terminal. A digital monitoring circuit includes a second data link interface, a second controller, a communications bridge and a multiplexer. The second data link interface is coupled to the gateway interface to provide bidirectional communication of data. The second controller includes a second link terminal, a digital group select terminal and a controller bus terminal, which is coupled to the second data link interface. The communications bridge has a bridge communication terminal and an input/output terminal, in which the bridge communication terminal is coupled to the controller bus terminal. The multiplexer has an address terminal, a multiplexer output terminal and a plurality of digital sensor terminals, in which the address terminal is coupled to the digital group select terminal, and the multiplexer output terminal is coupled to the input/output terminal.

Another example monitoring system includes a gateway configured to communicate information and commands. A computing apparatus is in communication with the gateway and configured to send commands to and receive information from the gateway. An analog monitoring circuit includes a first data link interface, a first controller, a driver network, an analog-to-digital converter, and a switch network. The first data link interface is configured to provide bidirectional communication between the gateway and the analog monitoring circuit. The first controller is configured to control the analog monitoring circuit and to return response data responsive to the commands received through the first data link interface. The driver network is configured to connect a respective sensor group to the switch network responsive to a sensor group select signal provided by the first controller. The analog-to-digital converter is configured to convert signals at a plurality of analog inputs to respective digital signal at a respective digital output. The switch network has a plurality of analog sensor terminals, and the switch network is configured to couple one or more of the analog sensor terminals to respective analog inputs of the analog-to-digital converter responsive to a sensor select signal provided by the first controller. A digital monitoring circuit includes a second data link interface, a second controller, a multiplexer, and a communications bridge. The second data link interface is configured to provide bidirectional communication between the gateway and the digital monitoring circuit. The second controller is configured to control the digital monitoring circuit and to return response data responsive to commands received through the second data link interface. The multiplexer is configured to couple a respective digital sensor group to an output of the multiplexer responsive to a digital group sensor select signal provided by the second controller. The communications bridge is configured to control reading one or more sensors on a selected sensor group responsive to a sensor identification signal provided by the second controller.

BRIEF DESCRIPTION OF THE DRAWINGS

FIG. 2 is a schematic diagram of an example sensor cable.

FIG. 3 is an example of an analog sensor cable.

FIG. 4 is a cross-sectional view of the sensor cable of FIG. 3.

DETAILED DESCRIPTION

This disclosure relates to remote monitoring systems and methods, such as for monitoring the condition of bulk solids, such as agricultural grain, pelletized materials (e.g., feed, wood pellets, and fertilizer) and equipment. As disclosed herein, the systems and methods disclosed herein integrate disparate analog and digital monitoring technologies, which are configured to sense and/or monitor one or more conditions of the condition of bulk solids, pelletized and associated equipment, and enable such technologies to be managed and controlled seamlessly by one or more users.

Figure 1:
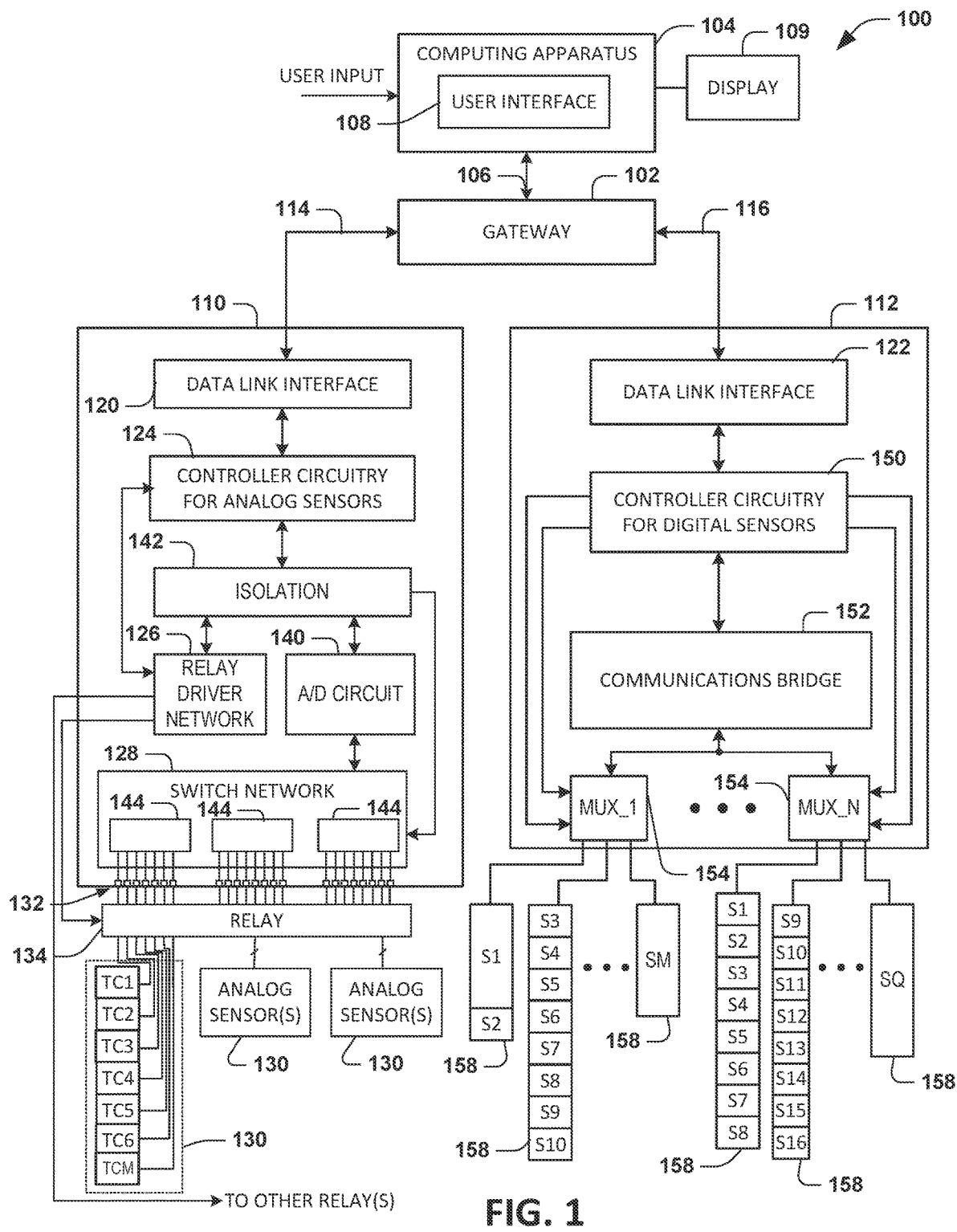
FIG. 1 is a block diagram showing an example of a monitoring system.

FIG. 1 is a block diagram showing an example of a monitoring system 100. The monitoring system 100 includes a gateway 102 and one or more computing apparatuses 104 in communication with the gateway. For example, the remote computing apparatus 104 is a desktop computer, a notebook computer, a tablet computer, cellular telephone. The computing apparatus 104 is coupled to the gateway 102 through a communications link 106. The communications link 106 can provide a communications path through one or more networks, which can include local area networks (LANs), wide area networks (WANs, e.g., the Internet) or a combination of various network infrastructures. The communications link 106 further can use one or more of wireless data communications (e.g., Bluetooth, WiFi, cellular data) and/or communications over physical paths (e.g., electrically conductive wires or traces and/or optical fibers).

The computing apparatus 104 is configured to send commands to and receive information from the gateway, such as in response to a user input provided through a user interface 108. The computing apparatus 104 can include an application programmed with instructions to issue one or more commands and/or requests to one or more sensors or other circuitry through the gateway 102 as well through any other parts of a communications infrastructure. The application can include instructions executable by a processor of the remote computing apparatus 104 to perform various monitoring and control functions, such as described herein. In another example, the application (or a portion thereof) can be implemented on a computing cloud to perform such functions.

The computing apparatus 104 can also include a display 109. The display 109 can be coupled to a video interface (e.g., hardware and software) of the computing apparatus 104 through a cable or the display can be integral with the computing apparatus. There can be various different types of computing apparatuses that can be used, such as described herein. The hardware and software implemented by the computing apparatus 104 (or in a computing cloud) are configured to control output data (e.g., information and graphics) that is provided to the display 109 for visualization. For example, the display 109 can include one or more of a monitor, projector, virtual reality headset or other type of display device to display information, such as text and/or graphics representative of information from sensors. The display can also display an interactive representation of the user interface 108. The computing apparatus 104 can also include or be coupled to one or more input devices (not shown), such as a pointing device (e.g., a mouse or touch screen) and/or other input device (e.g., a keyboard or keypad).

The gateway 102 is also configured to communicate with one or more analog monitoring circuits 110 and one or more digital monitoring circuits 112 through bidirectional communication links, shown at 114 and 116 respectively. While for ease of illustration two links 114 and 116 are shown, the links can include a number of one or more connections depending on the communications infrastructure between the computing apparatus and the respective monitoring circuits 110 and 112. The gateway 102 and the monitoring circuits 110 and 112 are configured (e.g., they include circuitry) to communicate through the links 114 and 116 using a data communications protocol. For example, each of the monitoring circuits 110 and 112 includes a data link interface 120 and 122 configured to provide for bi-directional data communications with the gateway 102. The data link interfaces 120 and 122 can implement a communications protocol, such as a serial communications protocol (e.g., RS-485) or another standard. The gateway 102 also includes one or more communications interfaces to communicate information and commands with the data link interfaces 120 and 122 through the respective links 114 and 116.

In one example, the links 114 and 116 are configured to communicate using wireless data communications (e.g., Bluetooth, XBee, Zigbee, DigiMesh, cellular data, etc.). For the example of using point-to-point or star wireless communications, the links 114 and 116 can also include an arrangement of repeaters depending on the distance and type of connections between the gateway 102 and the monitoring circuits 110 and 112. Other forms of wireless communication can be used to communicate with the monitoring circuits 110 and 112. In systems using wireless communication links at 106 and/or 114 and 116, each of the remote analog and digital circuits 110 and 112 can be electrically isolated on the communication side from every other switch in the system 100. This provides for added protection and isolation from electrical transient conditions, such as lightning strikes and power surges that are frequent in many environments. Additionally, or alternatively, the links 114 and 116 can implement data communications through a physical path.

As described herein, the gateway 102 is configured to concurrently wirelessly transmit outgoing software commands from the computing apparatus 104 to the monitoring circuits 110 and 112 through the communication links 114 and 116, and also receive information through the communication links from one or more of the monitoring circuits 110 and 112. The monitoring circuits 110 and 112 are configured to execute a predefined set of commands and requests issued by the remote computing apparatus 104, which can be the same commands and requests for both performing respective functions at the analog and digital monitoring circuits. Thus, from a perspective of the user as well as the gateway 102, the same commands are used regardless of whether the sensors are analog or digital sensors. The monitoring circuits 110 and 112 thus are configured to control (e.g., turn on) one or more switches, read sensor data from a group of one or more sensors and transmit sensor information back to the gateway responsive to respective commands that are issued. The common set of commands thus facilitates scalability and replacement of monitoring circuits 110 and 112 as well as components (e.g., switches and/or sensors) that can be coupled to the respective monitoring circuits.

As an example, the analog monitoring circuit 110 includes controller circuitry 124 (also referred to herein as a controller). The controller 124 includes a link terminal coupled to the data link interface, such as through a bus having one or more wires or conductive traces, for receiving and sending data. In an example, the controller 124 is a microcontroller having one or more processing cores and memory. The controller 124 is configured to control the analog monitoring circuit 110, including communication of commands and information and executing commands to perform sensing related functions.

The analog monitoring circuit 110 also includes a relay driver network 126 and a switch network 128. The controller 124 is coupled to the relay driver network 126 through a group address terminal and is coupled to the switch network through a switch select terminal. For example, the controller 124 is configured to provide a group select signal at the group address terminal to command the relay driver network to connect a group of one or more analog sensors (also referred to as a sensor group) 130 to the respective terminals 132 of the switch network 128. The relay driver network 126 can include an arrangement of driver circuits, each having a driver output coupled to a relay circuit 134. Each relay circuit 134 can be coupled between one or more analog sensor groups 130 and respective switch terminals 132. The relay driver network 126 is configured to activate a selected relay in the relay circuit 134 responsive to the group select signal (provided by the controller) to connect the sensors in the selected sensor group to respective terminals 132 of the switch network 128. In this way, only sensors in a currently selected sensor group (or groups) are coupled to the switch network to enable reading of sensor information from such sensors. The analog monitoring circuit 110 can include any number of relays 134, which can be configurable according to the number relays implemented in the relay circuit and the number of sensor groups 130. Alternatively, or additionally, additional instances of the analog monitoring circuit 110 can be added to the system 100 for increased sensing capacity.

As mentioned, each sensor group 130 can include one or more sensors. Each sensor can be configured to sense (e.g., measure) a condition, such as temperature, moisture. In the example of FIG. 1, three sensor groups 130 are shown, each of which can include a number of sensors, shown as temperature sensors TC1 through TCM for a respective sensor group 130, where M is a positive integer denoting the number of sensors. Various numbers and types of sensors can be implemented in a respective sensor group 130, which can be the same or different types of sensors per group.

In an example, a sensor group 130 is implemented as a temperature cable that includes a plurality of thermocouples (e.g., type-T thermocouples) configured to provide an analog voltage that is representative of temperature, which can be correlated back to the temperature (e.g., by the controller 124). Examples of analog sensor cables that can be used in the systems and methods disclosed herein are commercially available from Rolfes @Boone of Boone, Iowa. Other types of sensors and cables can be used in other examples. The analog monitoring circuit 110 can also be coupled to other types of sensors, such as hazard monitoring sensors. Examples of some hazard monitoring sensors include belt alignment sensors, motion speed, and probe or surface type temperature sensors. Other types of analog sensors can also be used depending on objects being monitored and/or conditions thereof to be sensed.

The switch network 128 has a switch address terminal coupled to the switch select terminal of the controller 124. In the example monitoring circuit 110 of FIG. 1, the switch network 128 is coupled to the controller 124 through an analog-to-digital (A/D) converter circuit 140 and isolation circuitry 142. The isolation circuitry 142 is configured to isolate the controller 124 from the switch network 128, relay 134 and sensors 130, which typically operate at higher voltages and currents. The switch address terminal can be coupled to a corresponding terminal of the isolation circuitry to receive a switch select signal, which has a value to specify one or more switches to activate for reading sensor information. The switch network 128 can include a plurality of switch circuits 144 coupled between an analog input of the A/D circuit 140 and the plurality of analog sensor terminals 132. Each switch circuit 144 can include an arrangement of switches (e.g., transistors) that are independently controllable. The switch network 128 thus is configured to couple one or more selected sensors to the analog input of the A/D circuit 140 responsive to a switch select signal received at the switch address terminal. As described herein, the switch select signal is provided by the controller 124 responsive to a command received from gateway 102.

The A/D circuit 140 has an output coupled to a data terminal of the controller 124, such as through the isolation circuitry 142. The A/D circuit 140 is configured to convert analog signals received at its analog input to corresponding digital signals. For example, one or more selected sensors of a selected sensor group 130, which are connected to the switch output through the relay 134 and switch network 128, provides analog voltage signals representative of a measured condition (e.g., temperature or moisture of bulk solids). The A/D circuit 140 reads the voltage provided by the one or more respective analog sensors and provides a corresponding digital value (e.g., a multibit value) to the controller 124. The controller 124 is configured to determine a measure of the sensed condition (e.g., temperature or moisture) based on the digital value of the sensor measurement, such as by correlating the digital value to measurement in appropriate units. To determine temperature from a thermocouple voltage, an additional temperature sensor can be implemented on the circuit 110 to provide a reference temperature.

The analog as well as digital sensor readings can be implemented sequentially or in parallel depending on the command(s) received by the controller 124, such as in response to a user input at the computing apparatus 104. In an example, the command can specify a command type (e.g., read temperature or read moisture or read speed or read position) and an object of the command. The object of the command, which is being instructed by the command, can include data identifying a sensor group and one or more sensors in the identified sensor group that is to implement the command. As an example, to read temperature of a second sensor in a first sensor group a command can be RT 1-2, where RT specifies a command to read temperature, "1" identifies a first sensor group (e.g., sensor cable) and "2" specifies the sensor number two of the first sensor group. Other command formats can be used in other examples, which can include the same or different commands. The commands can be issued from the computing apparatus 104 based on programmable settings for the system 100, which can be provided automatically (e.g., periodically or intermittently) or manually responsive to a user input. In an example, when the application is accessed (e.g., opened or invoked) at the computing apparatus 104, the application can be programmed to automatically issue commands to all sensors (or a prescribed set of sensors) to receive sensor data and provide a current (e.g. up to date) set of sensor data for the entire system 100.

The digital monitoring circuit 112 is configured to perform a similar sensing function as the analog monitoring circuit 110 in response to the same set of commands issued through the gateway 102 by the computing apparatus 104. The digital monitoring circuit 112 includes a controller 150 having a link terminal coupled to the data link interface 122. The controller 150 is thus configured to receive and send information and commands through the gateway 102, similar to as described for the analog monitoring circuit 110. The controller 150 is also configured to control the sensing and other functions implemented by the digital monitoring circuit 112.

The digital monitoring circuit 112 includes a communications bridge 152 and a multiplexer 154. The communications bridge is coupled between the multiplexer 154 and the controller 150. The multiplexer 154 can include one or more multiplexer circuits (shown as multiplexers 1 to N, where N is a positive integer), each having input terminals 156 to which respective digital sensors can be coupled. For example, a group of one or more digital sensors (also referred to as a digital sensor group) 158 can be coupled to each of the multiplexer input terminals 156. In the example of FIG. 1, one sensor group is shown having two digital sensors S1 and S2, another sensor group has 8 digital sensors S3-S10 and another sensor group has one digital sensor SM. As mentioned, each sensor group can include one or more digital sensors, each configured to sense a condition and provide a digital signal having a value representative of the sensed condition. The multiplexer circuits 154 also have address terminals coupled to a sensor group select output of the controller 150, such that the multiplexers 154 are configured to couple one or more respective sensors to the communication bridge 152 responsive to digital group select signal (e.g., provided by the controller 150) at the address terminal. For example, the digital group select signal has a value (e.g., a multibit ID or address) identifying a sensor group coupled to the digital monitoring circuit 112. The controller 150 can provide the digital group select signal responsive to parsing a command received from the gateway. As described herein, the command can be provided responsive to a user input instruction at the computing apparatus, which is sent to the gateway for specifying a sensing function to be performed by one or more sensors.

As an example, sensors S3-S10 can be implemented as a digital temperature cable that includes a plurality of temperature sensors, each of which is a digital signal having a value (e.g., a multibit value) representative of temperature. The digital sensor cable can include any number of digital sensors, such as an arrangement of digital temperature sensors distributed evenly along the length of the cable. Examples of digital sensor cables that can be used as the sensor groups 158 are the OPI temperature and moisture cables commercially available from OPI Systems Inc. of Calgary, Alberta, Canada. Other digital sensor cables or individual digital sensors (e.g., hazard monitoring sensors) can also be used in other examples. Examples of some digital hazard monitoring sensors include belt alignment sensors, motion speed, and probe or surface type temperature sensors.

The communication bridge 152 has a communications terminal (e.g., a digital bus) coupled to the controller 150 and an input/output terminal (e.g., another digital bus) coupled to the multiplexer 154. As an example, the bus between the controller 150 and the communication bridge 152 is a bidirectional bus, such as an I2C bus. Other bus structures implementing other protocols can also be used. The bus between the communication bridge 152 and the multiplexer 154 can be a multi-drop bus, such as a micro-LAN (e.g., implemented according to the 1-WIRE bus protocol of Analog Devices, Inc. of Wilmington, MA). The communication bridge 152 is configured to read one or more digital sensor values from one or more digital sensors 158 responsive to a read command provided by the controller 150. The digital sensors being read can be coupled to the input/output bus through the multiplexer 154 that has been activated responsive to the digital sensor group signal. The communications bridge 152 is further configured to provide the one or more digital sensor values to the controller 150 (e.g., through the bus between controller 150 and communication bridge 152) responsive to the sensor read command. As described herein, the controller 150 can be configured to provide the sensor read command to the communication bridge 152 responsive to a command received from the gateway 102.

In view of the foregoing, it should be appreciated that the system 100 can utilize both analog and digital sensing technologies seamlessly to implement monitoring of bulk products and related equipment. Each of the analog and digital circuits 110 and 112 can decode selection commands and transfer sensor data back to the computing apparatus 104 for display. Each of the analog and digital circuits 110 and 112 can also implement switching circuitry configured to access sensor information from respective sensors (e.g., temperature information from temperature cables) and communicate the sensor information back to the computing apparatus as directed by its executable instructions. In addition, the analog monitoring system 110 is configured to convert selected analog measurement signals (e.g., thermocouple temperature signals) to a digital signal. In the case of the digital monitoring system 112, there is no need to convert the digital temperature signals.

In some examples, the monitoring system 100 is unique in that it can simultaneously monitor Industry standard, Type "T" thermocouple temperature cables as well as cables that use digital 1-wire sensor technology. This feature provides a customizable solution to the marketplace to meet a variety of needs that vary for different facilities. The circuits 110 and 112 can further implement a modular design to allow users to add on temperature monitoring cables or other sensors according to user requirements. For example, as digital sensor cables might fail, the system allows users to replace the failed digital sensor cables with analog sensors that can be connected to terminals of the analog sensor circuit 110.

The system 100 also provides a secure wireless "web" of communication that permits all the various remote switches (thermocouple or digital) to become a protected wireless community through the central gateway. The user can thus monitor each of the analog and digital monitoring circuits locally through an onsite network, or remotely (e.g., using an app on a computing apparatus 104) through cloud services on a variety of different mobile platforms.

In some examples, the analog monitoring circuit 110 can be implemented in a dual compartment NEMA 4 steel enclosure that segregates the splice compartment from the main electronic components. Splice connections from sensor cables can terminate at conduit attachments in a lower splice compartment. An upper main electronic compartment of the enclosure can be moisture isolated from the splice compartment with a moisture impervious epoxy barrier and an isolated closed foam, door seal. The electronics compartment houses the analog circuit 110, which can be implemented on an arrangement of circuit boards, such as modular cards. In an example, each of the cards can be configured to selectively connect up to 21 or more analog sensor (e.g., temperature cable) outputs, and can include relay circuits to switch up to three sensor groups per card. For example, both the analog circuits 110 and relays 134 are implemented as modular cards configured to plug into a backplane by individual card edge connections for ease of maintenance and troubleshooting.

FIG. 2 is a simplified diagram showing an example of sensing cable 200, such as can be used to represent an analog or digital sensing cable 130 or 158. The cable 200 includes a plurality of sensors 202 distributed along its length. The length and number of sensors 202 can vary depending on application requirements.

FIGS. 3 and 4 depict an example of an analog sensor cable 300, which can be used to implement the sensing cable 130 of FIG. 1. The cable 300 includes connectors 302 and 304 at respective ends of the cable. Various types of connectors or other means of attachment can be used at 302 and 304. A leadwire can extend from one end of the cable, such as a top (e.g., proximal) end thereof near connector 302. The leadwire 306 can terminate in an arrangement of wires coupled to each of the analog sensors (e.g., sensors 202). The connector 304 at the distal end can include a connector or a weighted fixture to anchor the cable at an installed position.

FIG. 4 shows a cross-sectional view of the example cable 300. The cable 300 includes an analog sensor (e.g., thermocouple) bundle 310, a strain member 312, and outer covering 314 and sensing points (not shown). The inner strain member (e.g., steel rope) 312 provides strength against tensile and lateral forces encountered in stored grain vessels. The sensor bundle 310 contains the thermocouple reading points needed to monitor the bulk product (e.g., grain). The outer covering (an insulating over jacket) 314 provides a resilient and durable protective cover that binds the strain member and the thermocouple bundle into a single unit. This covering also protects the thermocouple bundle from abuse and abrasion. Temperature cables contain the individual thermocouples (e.g. type T thermocouples) at respective sensing points, which are distributed at regular spatial intervals along its length. This puts reading points evenly distributed throughout the mass of bulk products. Examples of analog sensor cables that can be used in the systems and methods disclosed herein are commercially available from Rolfes @Boone of Boone, Iowa.

Figure 5:
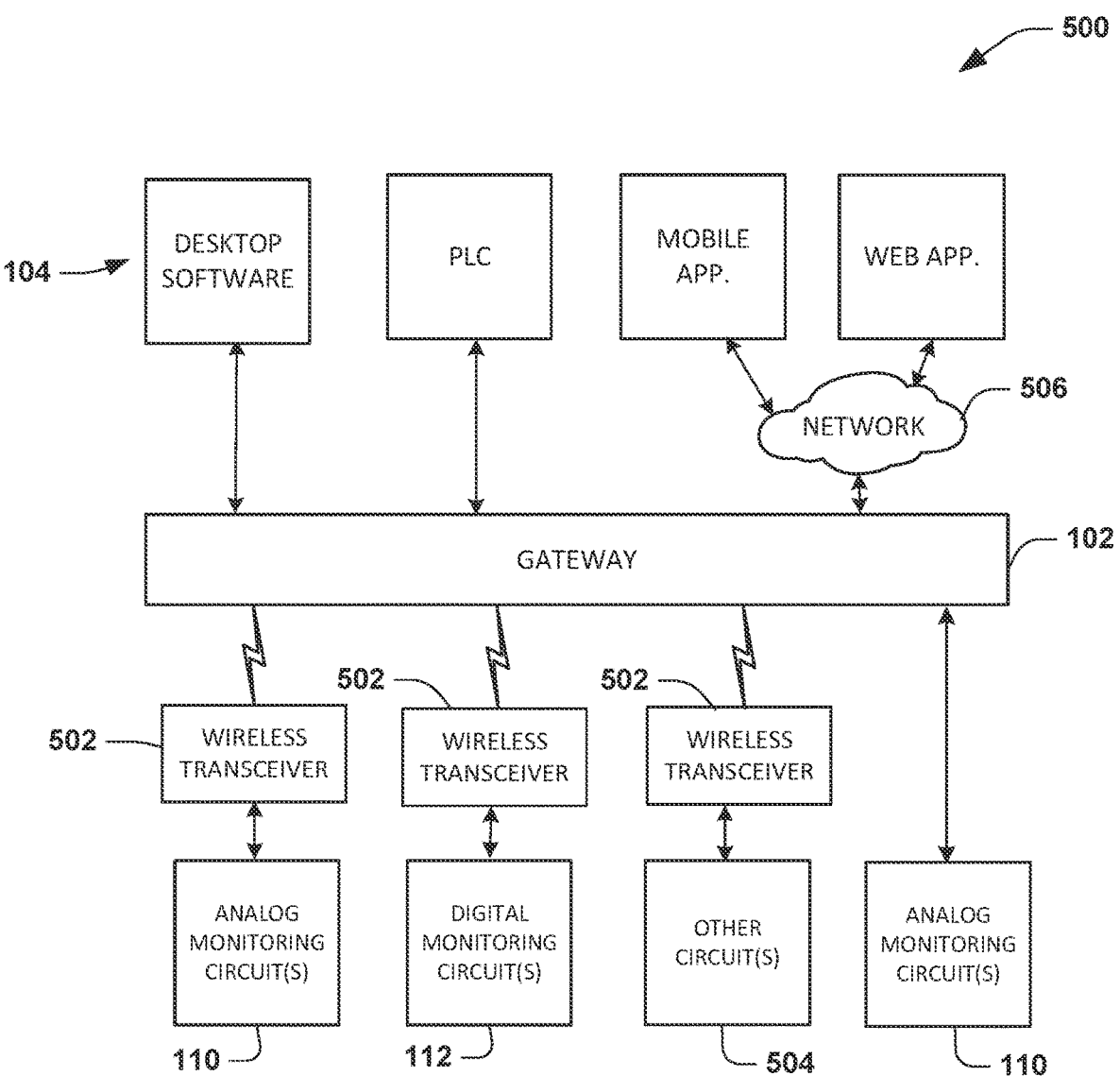
FIG. 5 is a high-level block diagram of an example monitoring system.

FIG. 5 is a high-level block diagram showing another example of a monitoring system 500. The system 500 depicts a useful example configuration for the system 100. Accordingly, FIG. 5 refers to parts already introduced in FIG. 1 by the same reference numbers used in FIG. 1. The system 500 also shows wireless transceivers (e.g., Xbee radios) 502 coupled between some of the monitoring circuits 110, 112, another monitoring circuit 504 and the gateway 102. The wireless transceivers can be part of the monitoring circuits or the monitoring circuits can be coupled to the wireless transceivers through a link (e.g., a cable).

FIG. 5 also shows various types of application environments for one or more computing apparatuses 104 that can be used, individually or in any combination, to monitor and control the sensing and other functions implemented by the system 500. For example, the computing apparatuses 104 can be implemented as desktop software (e.g., running in a desktop or laptop computer), a programmable logic controller (PLC), a mobile app (e.g., running on a smartphone or tablet computer) and/or a web application (e.g., running on web server or computing cloud). Other types of computing apparatuses 104 can also implement apps or applications for performing the monitoring, control and other functions described herein. Each computing apparatus 104 running the application can include a physical layer configured to be coupled to the analog and digital monitoring circuits 110 and 112 through the gateway 102, directly, or through another network (e.g., a LAN or WAN, such as the Internet) 506. For example, the mobile app and the web app, running on respective computing apparatuses, can be coupled to the gateway 102 through a network infrastructure 506, such as including the Internet. The physical communications layer implemented by the respective computing apparatuses 104 can include a physical link (e.g., wires and/or optical fiber) and/or wireless link. In the system 500, the gateway can be implemented with a local network, such as implementing Ethernet or other network topology. For example, the various types of computing apparatuses and/or applications being executed thereby (e.g., mobile app and the web app) can be configured to an IP address of the gateway. Also, or as an alternative, the wireless transceivers 502 can be configured to establish one or more corresponding wireless networks through which the gateway 102 and respective monitoring circuits 110, 112 and 504 can communicate. Additionally, or alternatively, one or more of respective monitoring circuits 110, 112 and 504 can be coupled to the gateway through a physical link (e.g., a single or multiconductor communications interface). After the network(s) have been configured, the sensors and/or other components associated with each of the respective monitoring circuits 110, 112 and 504 can be identified and assigned and identifier (e.g., an address) for communication, such as described herein.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

While particular details of various example embodiments have been described, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

What is claimed is:

1. A monitoring system, comprising:
a gateway having at least one interface configured to communicate information and commands;
a computing apparatus in communication with the gateway and configured to send commands to and receive information from the gateway;
an analog monitoring circuit, comprising:
    a first data link interface coupled to the gateway interface to provide bidirectional communication of data;
    a first controller including a first link terminal, a group address terminal, a switch select terminal and a data terminal, the first link terminal being coupled to the first data link interface;
    a driver network including a plurality of driver outputs and an address input terminal, the address input terminal being coupled to the group address terminal;
    an analog-to-digital converter including an analog input and a digital output, the digital output coupled to the data terminal; and
    a switch network having a switch address terminal and a plurality of analog sensor terminals, the switch network including plurality of switches coupled between the analog input and the analog sensor terminals, the switch address terminal coupled to the switch select terminal; and a digital monitoring circuit, comprising:
    a second data link interface coupled to the gateway interface to provide bidirectional communication of data;
    a second controller including a second link terminal, a digital group select terminal and a controller bus terminal, which is coupled to the second data link interface;
    a communications bridge having a bridge communication terminal and an input/output terminal, the bridge communication terminal being coupled to the controller bus terminal; and
    a multiplexer having an address terminal, a multiplexer output terminal and a plurality of digital sensor terminals, the address terminal coupled to the digital group select terminal, and the multiplexer output terminal being coupled to the input/output terminal.

2. The system of claim 1, wherein the analog monitoring circuit further comprises an analog sensor group of one or more analog sensors, in which each of the analog sensors in the analog sensor group has a respective sensor output coupled to a respective one of the analog sensor terminals.

3. The system of claim 2, further comprising a relay circuit having a control input coupled to a respective one of the driver outputs, the relay circuit being coupled between the analog sensor group and the respective analog sensor terminals.

4. The system of claim 3, wherein at least some of the analog sensors are distributed along an elongated cable.

5. The system of claim 2, wherein at least some of the analog sensors include at least one of an analog moisture sensor or a thermocouple.

6. The system of claim 1, further comprising a plurality of digital sensors, in which one or more of the digital sensors have a connector coupled to a respective one of the digital sensor terminals.

7. The system of claim 6, wherein one or more of the digital sensors include multiple sensors integrated in an elongated cable having the connector coupled to the respective one of the digital sensor terminals.

8. The system of claim 6, wherein the digital sensors include at least one of a moisture sensor or a temperature sensor.

9. The system of claim 1, wherein the driver network is configured to switch a sensor group to a respective one of the plurality of switches responsive to a device select signal at the address terminal, and
wherein the switch network is configured to couple the analog input with a respective analog sensor terminals responsive to a sensor signal at the switch address terminal.

10. The system of claim 9, wherein the first controller is configured to provide a sensor group select signal at the address terminal and a sensor select signal at the switch select terminal responsive to a command received at the first link terminal, the command being provided responsive to a user input instruction provided to the gateway specifying at least one device and sensor thereof.

11. The system of claim 9, wherein the device select signal has a value identifying a selected group of one or more analog sensors coupled to the analog monitoring circuit, and
wherein the sensor signal has a value identifying one or more of the respective analog sensors in the selected group.

12. The system of claim 1, wherein the multiplexer is configured to couple a respective digital sensor terminal to the input/output terminal responsive to a digital group select signal received at the address terminal, and wherein the communications bridge is configured to read one or more digital sensor values from a digital sensor group coupled to the respective digital sensor terminal and provide the one or more digital sensor values to the controller bus terminal responsive to a sensor read command received at the bridge communication terminal.

13. The system of claim 12, wherein the second controller is configured to provide the digital group select signal to the digital group select terminal and provide the sensor read command to the controller bus terminal responsive to parsing a command received at the second link terminal from the gateway, the command being provided responsive to a user input instruction provided to the gateway specifying a function to perform, a sensor group and at least one sensor of the digital sensor group.

14. The system of claim 12, wherein the digital group select signal has a value identifying a respective group of one or more digital sensors.

15. A monitoring system, comprising:

a gateway configured to communicate information and commands;

a computing apparatus in communication with the gateway and configured to send commands to and receive information from the gateway;

an analog monitoring circuit, comprising:

a first data link interface configured to provide bidirectional communication between the gateway and the analog monitoring circuit;

a first controller configured to control the analog monitoring circuit and to return response data responsive to the commands received through the first data link interface;

a driver network configured to connect a respective sensor group to a switch network responsive to a sensor group select signal provided by the first controller;

an analog-to-digital converter configured to convert signals at a plurality of analog inputs to respective digital signal at a respective digital output;

the switch network having a plurality of analog sensor terminals, the switch network configured to couple one or more of the analog sensor terminals to respective analog inputs of the analog-to-digital converter responsive to a sensor select signal provided by the first controller; and a digital monitoring circuit, comprising:

a second data link interface configured to provide bidirectional communication between the gateway and the digital monitoring circuit;

a second controller configured to control the digital monitoring circuit and to return response data responsive to commands received through the second data link interface;

a multiplexer configured to couple a respective digital sensor group to an output of the multiplexer responsive to a digital group sensor select signal provided by the second controller; and a communications bridge configured to control reading one or more sensors on a selected sensor group responsive to a sensor identification signal provided by the second controller.

16. The system of claim 15, wherein the commands used by the analog and digital monitoring circuits are provided by the gateway according to a common schema, in which the common schema specifies a command function, a respective sensor group and one or more sensors of the sensor group specified in each of the respective commands.

17. The system of claim 15, further comprising:

an analog sensor group of one or more analog sensors, each of the analog sensors in the analog sensor group has a respective sensor output coupled to a respective one of the analog sensor terminals; and a plurality of digital sensors, in which one or more of the digital sensors are coupled to a respective one or more digital inputs of the multiplexer.

18. The system of claim 17, wherein at least one group of analog sensors comprises a thermocouple temperature cable having a plurality of analog temperature sensors, and one or more of the digital sensors include multiple sensors integrated in an elongated cable having a connector thereof coupled to a respective digital input of the multiplexer.

19. The system of claim 17, wherein the analog monitoring circuit further comprises a relay circuit having a control input coupled to a respective one of the group sensor outputs, the relay circuit being coupled between the analog sensors and the respective analog sensor terminals.

20. The system of claim 15, wherein the first controller is configured to provide a first sensor group select signal and the sensor select signal responsive to a first command instruction provided to the gateway, the first command instruction specifying at least one device and sensor coupled to the analog monitoring circuit, and wherein the second controller is configured to provide a second sensor group select signal and provide a sensor read command responsive to a second command instruction provided to the gateway, the second command instruction specifying a function to perform, a respective digital sensor group and at least one sensor of the respective digital sensor group.

* * * * *